United States Patent [19]

Olsen

[11] Patent Number: 4,685,462

[45] Date of Patent: Aug. 11, 1987

[54] METHOD AND APPARATUS FOR TREATMENT OF HYPOTHERMIA BY ELECTROMAGNETIC ENERGY

[75] Inventor: Richard G. Olsen, Pensacola, Fla.

[73] Assignee: The United States of America as represented by the Secretary of the Navy, Washington, D.C.

[21] Appl. No.: 768,072

[22] Filed: Aug. 21, 1985

[51] Int. Cl.$^4$ .............................................. A61N 1/04
[52] U.S. Cl. .................................. 128/422; 128/379; 128/804
[58] Field of Search ................ 128/422, 804, 1.5, 399, 128/402, 379

[56] References Cited

U.S. PATENT DOCUMENTS

| | | | |
|---|---|---|---|
| 96,044 | 10/1869 | Smith | 128/1.5 |
| 2,240,955 | 5/1941 | Mittlemann | 128/422 |
| 2,752,496 | 6/1956 | Martens | 128/422 |
| 3,738,367 | 6/1973 | Hardy | 128/379 |

FOREIGN PATENT DOCUMENTS 203466 10/1983 Fed. Rep. of Germany ...... 128/804

*Primary Examiner*—William E. Kamm
*Attorney, Agent, or Firm*—Robert F. Beers; Harvey A. David

[57] ABSTRACT

An apparatus and method for rewarming hypothermia victims utilizes mutually inductive first and second helical coils supported in spaced relation around a subject's torso, the combination of coils and subject having a resonant frequency in the 2 MHz to 20 MHz radio frequency range. An automatic tuner couples an RF generator to energize the coils at the resonant frequency. A portable version utilizes flexible coils on an insulating and spacing jacket having a zippered opening with conductive teeth to complete coil turns.

2 Claims, 3 Drawing Figures

METHOD AND APPARATUS FOR TREATMENT OF HYPOTHERMIA BY ELECTROMAGNETIC ENERGY

BACKGROUND OF THE INVENTION

This invention relates generally to the field of electromagnetic therapeutics. More particularly, the invention is directed to the generation and use of electromagnetic fields in interaction with a biological body to effect internal warming of the body in the treatment of severe hypothermia.

Hypothermia often results from prolonged exposure to cold under adverse conditions such as by immersion of personnel in water following boating accidents, downed aircraft, or the like. Once the "core" temperature of a person has fallen significantly below normal and a condition of severe hypothermia exists, that condition is not easily reversed and death often follows. Active central rewarming of the body is needed as quickly as possible and peritoneal dialysis by warming fluids has been the treatment of choice for severe hypothermia. However, since that is an invasive technique requiring substantial clinical support, peritoneal dialysis cannot be accomplished in remote field locations or aboard ships with limited medical facilities. Breathing warm, humidified air provides some deep body core heating, and there are devices commercially available for that purpose. Inhalation warming methods, however, are relatively slow and are best suited to treatment of mild hypothermia. Warm water immersion treatment is ineffective as there is a high risk that the rest of the body will warm up faster than the heart, which quickly leads to cardiac arrest.

A variety of devices and techniques are known for therapeutic treatment of cancers or other tumors by hyperthermia, i.e., unnaturally elevated body temperature, induced by electromagnetic wave energy at radio wave or microwave frequencies. These, again, have been limited to clinical settings, generally involve nonportable equipment, and require highly trained medical and technical personnel operating under carefully controlled conditions to avoid or minimize injury to healthy tissues because of the abnormally high temperatures involved. The various apparatus used in inducing such temperatures generally attempt to concentrate or focus energy on or at a localized tumer site. Because of that concentration, and because the SAR (specific absorption rate) of energy at the body surface is much more than that at the central portions of a subject's body, use of known hyperthermia apparatus for rewarming hypothermia victims would result in severe skin and outer tissue burns.

SUMMARY OF THE INVENTION

With the foregoing in mind, it is a principal object of this invention to provide a non-invasive apparatus and method for safely and relatively quickly bringing a person out of a severe hypothermic state.

Another important object of the invention is to provide a method and apparatus that is simple to use and can be carried out by apparatus that is sufficiently portable to permit use in remote locations and under considerably less than clinical conditions.

As another object the invention aims to provide electromagnetic apparatus for subjecting a hypothermia victim to internal heating by radio frequency waves, and wherein the apparatus is automatically adaptable to subjects of different size and mass.

As another object the invention aims to provide a practical radio frequency device which will provide heating substantially throughout a central body region containing the heart, will not cause disruptive EMI (electromagnetic interference) in aircraft systems, and in its most portable form can be readily donned by an ambulatory hypothermic casualty or easily attached to an unconscious victim and be safely used as first-aid in a rescue operation.

Other objects and many of the attendant advantages will be readily appreciated as the subject invention becomes better understood by reference to the following detailed description, when considered in conjunction with the accompanying drawings.

DESCRIPTION OF THE PREFERRED EMBODIMENT

Figure 1:
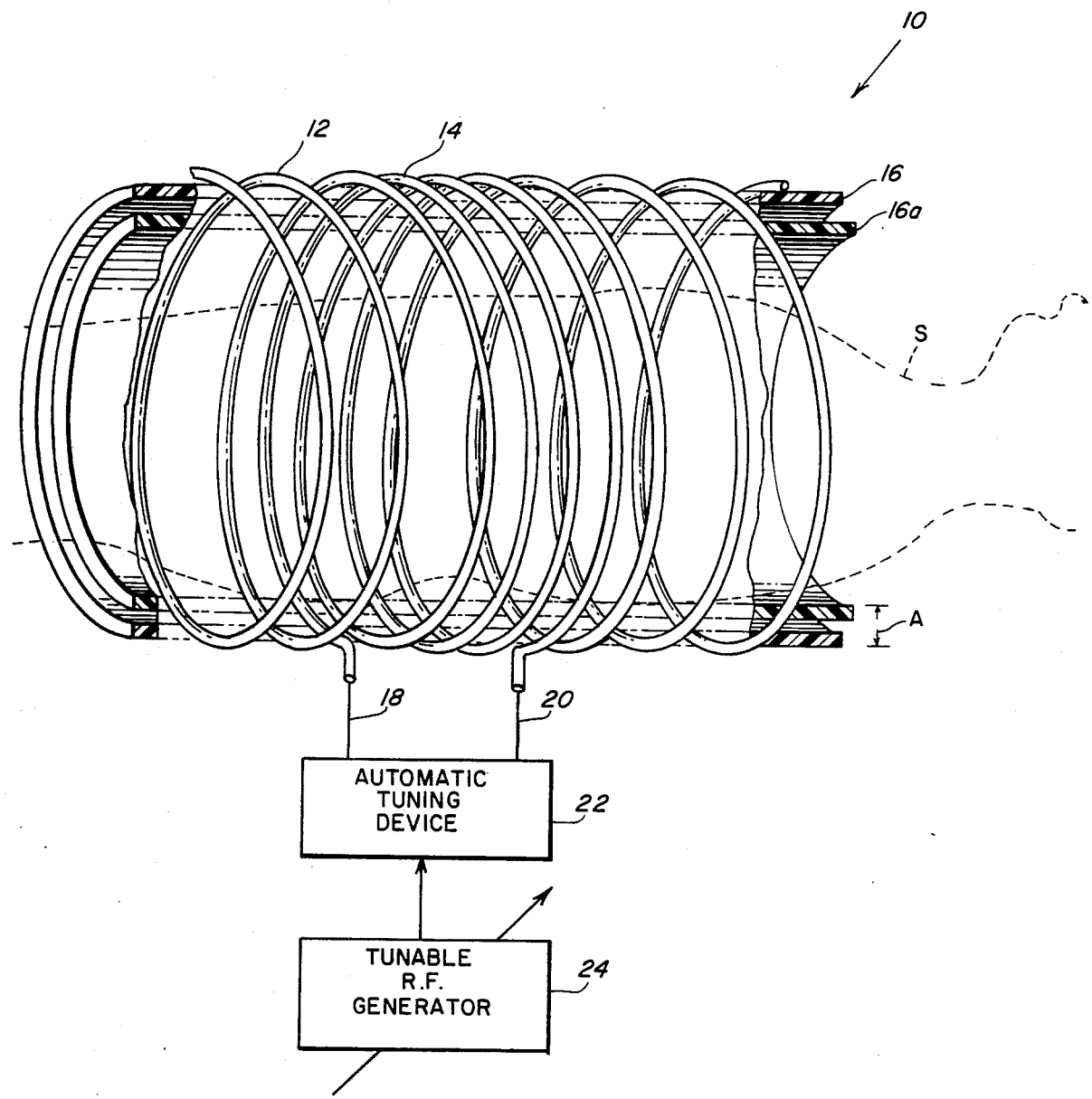
FIG. 1 is diagrammatic illustration of a hypothermia treatment apparatus embodying the present invention.

Referring to FIG. 1, the apparatus 10 comprises a large solenoid or helical coil 12 having a diameter sufficient for a subject to be placed inside the lumen with a predetermined minimum air gap A between the coil 12 and the subject S. The turns of the coil 12 are preferably formed of a metallic conductor that has considerable surface, e.g., copper tubing, and range in number from about four turns to sixteen turns, seven turns being shown in the exemplary embodiment of FIG. 1. The coil 12 is, in this example, electrically open-ended and is adapted to be energized with RF current by a mutually inductively coupled driver coil 14. The coil 14 is of similar material and diameter but has fewer turns, two in this example, that are inter-leaved with the central turns of the coil 12 so as to inductively couple therewith. The coils 12 and 14 are conveniently supported on a non-conductive tubular form means 16 having a concentric inner tubular member 16a for supporting the subject S within annular gap A.

The driver coil 14 has its opposite ends connected as shown by lines 18,20 to the output of an automatic tuning device 22 which couples that coil to a radio-frequency generator 24 having a power output capability (preferably variable) on the order of about 50 to 200 watts. Tests indicate that power can safely be applied at rates as high as 10 watts per kg mass of a subject at temperatures of below 30 degrees C. For a 70 kg subject, powers of 1000 watts are feasible. The lower power range of the exemplary embodiment is presently believed to provide adequate rewarming rates with a substantial margin of safety against burns. In the preferred form, an automatic tuning device 22, which may be in the form of switched capacitors and inductors, transforms the coil and subject impedance to a purely resistive load equal to the tunable RF generator output impedance. One suitable automatic frequency tuner (AFT) is the Model 490T-1 of the Collins Radio Division of Rockwell International Corporation of El Segundo, Calif.

The combination of coils 12,14 and subject S may be regarded as having an equivalent circuit composed of capacitances, resistances and inductances in a somewhat complex parallel resonance configuration. Operation at resonant frequency maximizes the warming effect with the minimum application of power, thereby reducing possibility of burns and minimizing stray radiations that could cause EMI (electromagnetic interference) with other electronic equipment.

Of course, the biological mass and makeup of different subjects will result in different resonant frequencies and this will be accommodated by the automatic tuning feature. Preferably, the size and numbers of the turns of the coils are selected to provide resonance in the range of about two to twenty MHz.

Figure 2:
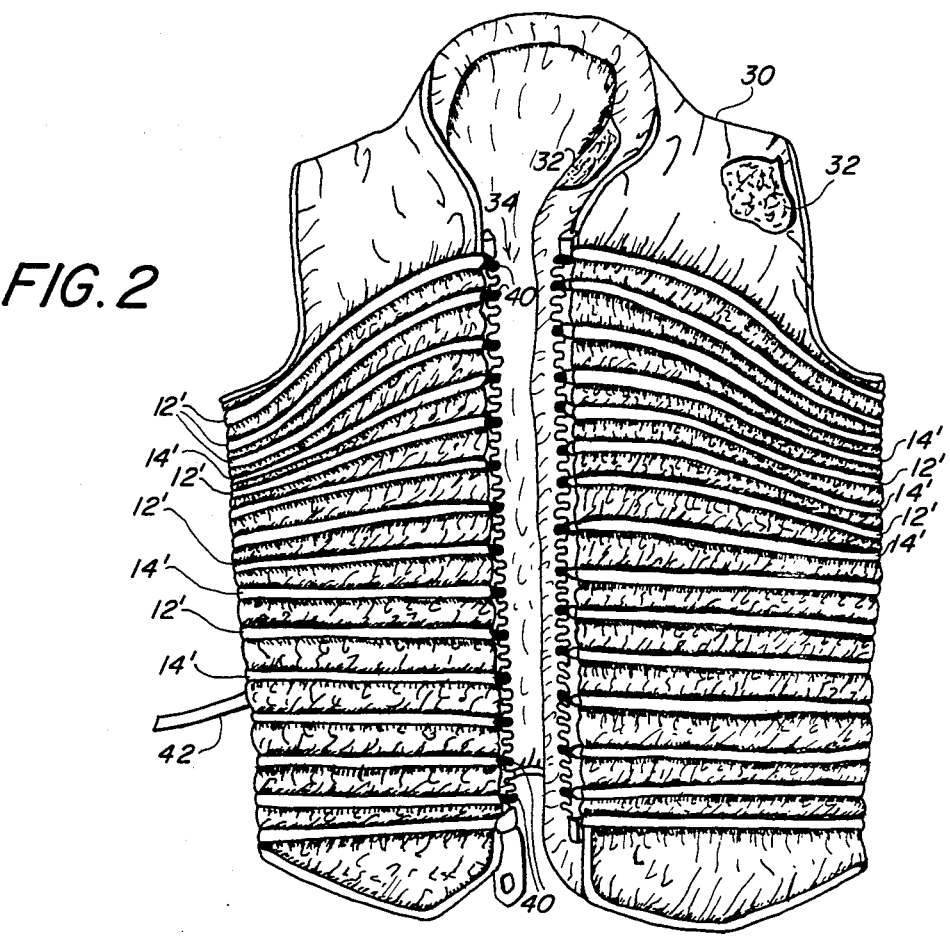
FIG. 2 is a front elevational view of a flexible coil and support structure for first-aid application of the invention to a hypothermia victim.
Figure 3:
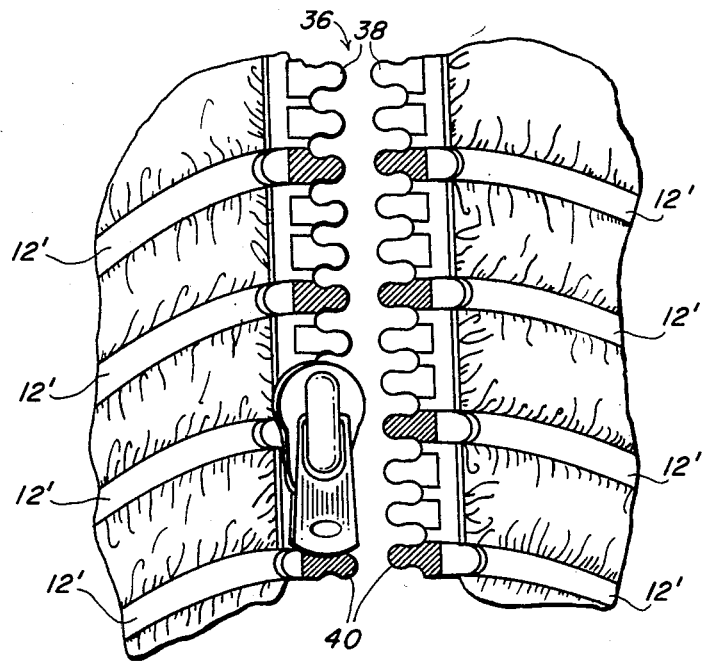
FIG. 3 is a fragmentary view, on an enlarged scale, illustrating structural detail of the coil and support of FIG. 3.

Referring now to FIGS. 2 and 3, an alternative embodiment of coil support and spacer means is provided that is particularly suited to first-aid applications of the invention. In this embodiment, flexible driven and driver coils 12' and 14', corresponding to coils 12 and 14 of FIG. 1, are fixed to a fabric jacket 30 having a lining or filling of non-conductive foam material 32 to ensure at least a predetermined minimum air gap between the coils and the subject while at the same time offering thermal insulation. The turns of coils 12' and 14' are conveniently formed of braided, flexible, electrically conductive shielding loom and are interruptable at the zippered opening 34 in the jacket 30 to facilitate donning thereof by or placing onto a hypothermia victim.

The zipper 36 is provided with non-conductive teeth 38 except where the coils 12', 14' intersect, at which locations the zipper comprises conductive teeth 40. When the zipper is closed, the conductive teeth 40 complete the turns of the coils 12' and 14'. An insulated flexible cable 42 carries conductors for connection of the coil 14' to the automatic tuning device 22. This embodiment permits an easily stored, portable, and readily applied apparatus for effecting rewarming by RF energy in remote locations or limited spaces as on aircraft, small boats or the like.

In carrying out the invention it is preferred that a minimum air gap of at least about 0.25" be preserved between the coils and the skin of the subject and that the coil 12 or 12' extend over most or all of the upper body portion containing the heart. The principal heat development is in about the central one-third of the length of the coil, but is sufficiently distributed to avoid dangerous localized heating while at the same time effectively reversing the hypothermic condition. Tests with animals have shown that a subject suffering severe hypothermia, such that the inner or core temperature has been reduced to as low as 35 degrees C., or lower, can be rapidly rewarmed in a matter of minutes to normal body temperature with no adverse effects.

Frequencies in the range of about 2 to 20 Mhz are suitable, and it will be understood that the actual resonant frequency of operation will be determined by the intrinsic combination of the coil and subject. For example, one practical device having a nine turn driven coil 12' operates at a frequency of 13.56 MHz when used on a 70 kg subject. A non-perturbing temperature probe can be used to monitor body temperature rise. In first-aid situations, a simple liquid crystal thermometer of the strip type that shows different colors for different temperatures is conveniently used on the skin of subject. Inasmuch as the SAR (specific absorption rate) of energy at the skin level is typically more than that at the center of the subject, monitoring of skin temperature to prevent possible burns also provides a substantial margin of protection against internal damage. With this in mind, a suitable window either as an opening or transparent portion can be provided in the jacket 30 to view a small area of skin and an applied liquid crystal thermometer strip.

Experiments have further shown that with the entire jacket and subject submerged in salt water, the apparatus functions to prevent heat loss in the subject. The invention contemplates the incorporation of radio frequency coils in garments other than for rewarming hypothermia victims, for example in diving suits for use in extremely cold conditions.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. Apparatus for rewarming a human subject from a state of severe hypothermia, said apparatus comprising:
   a helical first coil comprising a flexible electrical conductor formed into a plurality of turns, in the range of about 4 to 16 turns, so as to define a lumen for receiving the torso of said subject from about the waist to about the upper chest thereof so as to cover a zone including the heart of said subject, said first coil being electrically open-ended;
   a helical second coil comprising a flexible electrical conductor formed into at least one turn interleaved with turns of said first coil so that said first and second coils are mutually inductively coupled;
   support means comprising a flexible fabric jacket to which said coils are secured comprising flexible insulation and spacing material for maintaining a minimum predetermined spacing between said coils and said subject, said jacket having an opening at which said coil turns are interrupted to facilitate donning and zipper means comprising mating conductive teeth for electrically connecting interrupted portions of said turns when said zipper means is closed and non-conductive teeth disposed between said turns;
   said first and second coils being cooperable with said subject to form an alternating current resonant circuit having a characteristic resonant frequency in the range of about 2 MHz to about 20 MHz;
   an alternating current source comprising a radio frequency generator for generating alternating current at said characteristic resonant frequency;
   means connecting said alternating current source to said second coil for energizing thereof with said alternating current and inductively energizing said first coil at said resonant frequency whereby said subject is warmed throughout said zone.

2. an apparatus according to claim 1, and wherein:
   said first coil and said second coil comprise inductively coupled driven and driver coils, respectively;
   said means connecting said alternating current source to said second coil comprises automatic tuning means connected to said current source and to the ends of said driver coil and responsive to combined coil and subject impedance to provide a resistive load equal to the output impedance of said alternating current source at said resonant frequency.

* * * * *